: US006764844B1

(12) United States Patent
Lindahl et al.

(10) Patent No.: US 6,764,844 B1
(45) Date of Patent: Jul. 20, 2004

(54) DNA SEQUENCE ENCODING A NOVEL GLUCURONYL C5-EPIMERASE

(75) Inventors: Ulf Lindahl, Uppsala (SE); Jing-ping Li, Uppsala (SE)

(73) Assignee: Biotie Therapies, Corp. (FI)

(*) Notice: Subject to any disclaimer, the term of this patent is extended or adjusted under 35 U.S.C. 154(b) by 0 days.

(21) Appl. No.: 09/403,269

(22) PCT Filed: Apr. 17, 1998

(86) PCT No.: PCT/SE98/00703
§ 371 (c)(1),
(2), (4) Date: Oct. 18, 1999

(87) PCT Pub. No.: WO98/48006
PCT Pub. Date: Oct. 29, 1998

(30) Foreign Application Priority Data

Apr. 18, 1997 (SE) ............................................. 9701454

(51) Int. Cl.[7] .......................... C12N 9/90; C12N 15/00; C07H 21/04
(52) U.S. Cl. .................... 435/233; 435/320.1; 435/348; 435/252.33; 435/358; 435/365; 435/369; 435/252.3; 435/325; 435/233; 536/23.2; 536/23.5; 536/23.4
(58) Field of Search ............................... 536/23.4, 23.2; 435/320.1, 252.33, 252.3, 69.1, 325, 348, 365, 358, 366, 369, 233

(56) References Cited

U.S. PATENT DOCUMENTS

| 5,939,289 A | 8/1999 | Ertesvåg et al. ............... 435/72 |
| 6,372,477 B1 | 4/2002 | Jøosboe et al. ............. 435/233 |

FOREIGN PATENT DOCUMENTS

| JP | WO 01/38507 A1 | 5/2001 |
| WO | WO96/14425 | 5/1996 |
| WO | WO 98/48006 A1 | 10/1998 |

OTHER PUBLICATIONS

Voet et al. "Biochemistry", 2nd Ed., John Wiley and Sons, Inc., 1995.*
Xue et al. Cell 72(5):681–693 (1993).*
Wilson et al. Nature 368(6466):32–38 (1994).*
NCBI Entrez, GenBank Report, Accession No. AAF57373, from Adams, M.D. et al. (Mar. 2000).
Crawford, B.E. et al., "Cloning, Golgi Localization, and Enzyme Activity of the Full–length Heparin/Heparan Sulfate–Glucuronic Acid C5–epimerase", *J. Biol. Chem.* 276:21538–21543, The American Society for Biochemistry and Molecular Biology, Inc. (Jun. 2001).
Féthière, J. et al., "Crystal Structure of Chondroitin AC Lyase, a Representative of a family of Glycosaminoglycan Degrading Enzymes," *J. Mol. Biol.* 288:635–647, Academic Press (May 1999).
Dialog File 351, Accession No. 2001–381292/200140, Derwent WPI English language abstract for WO 01/38507 (May 31, 2001).
NCBI Entrez, GenBank Report, Accession No. P46555, from Sulston, J. (1994).
NCBI Entrez, GenBank Report, Accession No. AF043700, from Wilson, R. et al. (1998).
NCBI Entrez, GenBank Report, Accession No. AAF36018, from The C. elegans Sequencing Consortium et al. (1998).
Ron, D. et al., "Expression of Biologically Active Recombinant Keratinocyte Growth Factor. Structure/Function Analysis of Amino–Terminal Truncation Mutants," *J. Biol. Chem.* 268:2984–2988, American Society of Biochemistry Molecular Biology Inc. (1993).
NCBI Entrez, GenBank Report, Accession No. LO8483, from Xue, F. et al. (1993).
Database Biosis Biosciences Information Service, Database accession No. PREV200000122890, abstract for Hagner–McWhirter, A. et al., "Biosynthesis of herparin/heparan sulphate: Kinetic studies of the glucuronyl C5–epimerase with N–sulfated derivatives of the *Escherichia coli* K5 capsular polysaccharide as substrates," (Feb. 2000).
D–glucuronyl C5–epimerase amino acid sequence (EC 5.1.3.–), Accession No. 094923, Database EBI [Online] (May 1999).
Nagase, T. et al., "Prediction of the Coding Sequence of Unidentified Human Genes. XII. The Complete Sequences of 100 New cDNA Clones from Brain Which Code for Large Proteins in vitro," *DNA Res.* 5:355–364, Tokyo Kazusa DNA Research Institute and Universal Academy Press (1998).
D–glucuronyl C5–epimerase (EC 5.1.3.–) amino acid sequence (mouse), Accession No. Q9EPS3, Database EBI [Online] (Mar. 2001).
D–glucuronyl C5–epimerase (EC 5.1.3.–) amino acid sequence (bovine), Accession No. 018756, Database EBI [Online] (Jan. 1998).

(List continued on next page.)

Primary Examiner—Rebecca Puty
Assistant Examiner—David J Steadman
(74) *Attorney, Agent, or Firm*—Sterne, Kessler, Goldstein and Fox P.L.L.C.

(57) ABSTRACT

An isolated or recombinant DNA sequence coding for a mammalian, including human, glucuronyl C5-epimerase or a functional derivative thereof capable or converting D-glucuronyl acid (GlcA) to L-iduronic acid (IdoA); a recombinant expression vector comprising such DNA sequence; a host cell transformed with such recombinant expression vector; a process for manufacture of a glucuronyl C5-epimerase or functional derivative thereof capable of coverting GlcA to IdoA, comprising cultivation of a cell-line transformed with such recombinant expression vector; and a glucuronyl C5-epimerase or functional derivative thereof prepared by such process.

50 Claims, 2 Drawing Sheets

OTHER PUBLICATIONS

Kelley, L.A. et al., "Enhanced Genome Annotation Using Structural Profiles in the Program 3D–PSSM," *J. Mol. Biol.* 299:499–520, Academic Press (Jun. 2000).

Li, J.–p. et al., "Biosynthesis of Heparin/Heparan Sulfate. cDNA Cloning and Expression of D–Glucuronyl C5–Epimerase from Bovine Lung.," *J. Biol. Chem.* 272:28158–28163, The American Society for Biochemistry and Molecular Biology, Inc. (1997).

Malmström, A. et al., "Biosynthesis of Heparin. Partial Purification of the Uronosyl C–5 Epimerase," *J. Biol. Chem.* 255:3878–3883, American Society of Biochemistry and Molecular Biology Inc. (1980).

Hagner–McWhirter, Å. et al., "Biosynthesis of heparin/ heparin sulfate: kinetic studies of the glucuronyl C5–epimerase with N–sulfated derivatives of the *Esherichia coli* K5 capsular polysaccharide as substrates," Glycobiology 10:159–171, Oxford University Press (Feb. 2000).

Hagner–McWhirter, Å. et al., "Biosynthesis of heparin/ heparan sulphate: mechanism of epimerization of glucuronyl C–5," *Biochem J.* 347:69–75, London Portland Press On Behalf Of The Biochemical Society (Apr. 2000).

"Conformational flexibility: a new concept for explaining binding and biological properties of iduronic acid–containing glycosaminoglycans", B. Casu et al., *TIBS*, vol. 13 (Jun. 1988) pp. 221–225.

"Heparan sulfate: a piece of information", Markku Salmivirta et al., *The FASEB Journal*, vol. 10 (Sep. 1996) pp. 1270–1279.

"Proteoglycans: Structures and Interactions", Lena Kjellén et al., *Annul. Rev. Biochem.*, vol. 60 (1991) pp. 443–475.

"*Biosynthesis of Heparin/Heparan Sulfate: Purification of the $_D$–Glucuronyl C–5 Epimerase from Bovine Liver*", Patrick Campbell et al., *The Journal of Biochemical Chemistry*, vol. 269, No. 43 (Oct. 28, 1994) pp. 26953–26958.

* cited by examiner

SEQUENCE LISTING

<160> NUMBER OF SEQ ID NOS: 13

<210> SEQ ID NO 1
<211> LENGTH: 17
<212> TYPE: DNA
<213> ORGANISM: Human

<400> SEQUENCE: 1
gctgattctt ttctgtc                                                    17

<210> SEQ ID NO 2
<211> LENGTH: 13
<212> TYPE: PRT
<213> ORGANISM: Human
<220> FEATURE:
<221> NAME/KEY: PEPTIDE
<222> LOCATION: (5)..(5)

<223> OTHER INFORMATION: Amino acid 5 is Xaa wherein Xaa = any amino
      acid.

<400> SEQUENCE: 2

Pro Asn Asp Trp Xaa Val Pro Lys Gly Cys Phe Met Ala
1               5                   10

<210> SEQ ID NO 3
<211> LENGTH: 11
<212> TYPE: PRT
<213> ORGANISM: Human
<220> FEATURE:
<221> NAME/KEY: PEPTIDE
<222> LOCATION: (2)..(10)
<223> OTHER INFORMATION: Amino acids 2 and 10 are Xaa wherein Xaa = any
      amino acid.

<400> SEQUENCE: 3

Pro Xaa Asp Trp Thr Val Pro Lys Gly Xaa Phe
1               5                   10

<210> SEQ ID NO 4
<211> LENGTH: 8
<212> TYPE: PRT
<213> ORGANISM: Human
<220> FEATURE:
<221> NAME/KEY: PEPTIDE
<222> LOCATION: (4)..(4)
<223> OTHER INFORMATION: Amino acid 4 is Xaa wherein Xaa = any amino
      acid.

<400> SEQUENCE: 4

Pro Asn Asp Xaa Thr Val Pro Lys
1               5

<210> SEQ ID NO 5
<211> LENGTH: 15
<212> TYPE: PRT
<213> ORGANISM: Human
<220> FEATURE:
<221> NAME/KEY: PEPTIDE
<222> LOCATION: (1)..(11)
<223> OTHER INFORMATION: Amino acids 1, 2 and 11 are Xaa wherein Xaa =
      any amino acid.

<400> SEQUENCE: 5

Xaa Xaa Ile Ala Pro Glu Thr Ser Glu Gly Xaa Ser Leu Gln Leu
1               5                   10                  15

<210> SEQ ID NO 6
<211> LENGTH: 10
<212> TYPE: PRT
<213> ORGANISM: Human

<400> SEQUENCE: 6

Gly Gly Trp Pro Ile Met Val Thr Arg Lys
1               5                   10

<210> SEQ ID NO 7
<211> LENGTH: 8
<212> TYPE: PRT
<213> ORGANISM: Human

<400> SEQUENCE: 7

Phe Leu Ser Glu Gln His Gly Val
1               5

```
<210> SEQ ID NO 8
<211> LENGTH: 36
<212> TYPE: PRT
<213> ORGANISM: Human
<220> FEATURE:
<221> NAME/KEY: PEPTIDE
<222> LOCATION: (30)..(30)
<223> OTHER INFORMATION: Amino acid 30 is Xaa wherein Xaa = any amino
      acid.

<400> SEQUENCE: 8

Lys Ala Met Leu Pro Leu Tyr Asp Thr Gly Ser Gly Thr Ile Tyr Asp
1               5                  10                 15

Leu Arg His Phe Met Leu Gly Ile Ala Pro Asn Leu Ala Xaa Trp Asp
            20                 25                 30

Tyr His Thr Thr
        35

<210> SEQ ID NO 9
<211> LENGTH: 25
<212> TYPE: DNA
<213> ORGANISM: Human
<220> FEATURE:
<221> NAME/KEY: misc_feature
<222> LOCATION: (14)..(23)
<223> OTHER INFORMATION: Nucleotides 14, 20 and 23 are "n" wherein
      "n" = any nucleotide.

<400> SEQUENCE: 9
ccgaattcaa rgcnatgytn ccnyt                                    25

<210> SEQ ID NO 10
<211> LENGTH: 26
<212> TYPE: DNA
<213> ORGANISM: Human
<220> FEATURE:
<221> NAME/KEY: misc_feature
<222> LOCATION: (14)..(17)
<223> OTHER INFORMATION: Nucleotides 14 and 17 are "n" wherein "n" = any
      nucleotide.

<400> SEQUENCE: 10
ccgaattcga yytnmgncay ttyatg                                   26

<210> SEQ ID NO 11
<211> LENGTH: 25
<212> TYPE: DNA
<213> ORGANISM: Human
<220> FEATURE:
<221> NAME/KEY: misc_feature
<222> LOCATION: (11)..(11)
<223> OTHER INFORMATION: Nucleotide 11 is "n" wherein "n" = any
      nucleotide.

<400> SEQUENCE: 11
ccggatccgt ngtrtgrtar tccca                                    25

<210> SEQ ID NO 12
<211> LENGTH: 3085
<212> TYPE: DNA
<213> ORGANISM: Human
<220> FEATURE:
<221> NAME/KEY: CDS
<222> LOCATION: (73)..(1404)

<400> SEQUENCE: 12
tccaagctga attctcatag ctattccaaa gtctatgcac agagagcccc ttatcaccct   60
```

-continued

```
gatggtgtgt tt atg tcc ttt gaa ggc tac aat gtg gaa gtc cga gac aga       111
           Met Ser Phe Glu Gly Tyr Asn Val Glu Val Arg Asp Arg
            1               5                  10 gtc aag tgc ata agt ggg gtt gaa ggt gta cct tta tct aca cag tgg          159
Val Lys Cys Ile Ser Gly Val Glu Gly Val Pro Leu Ser Thr Gln Trp
 15              20                  25 gga cct caa ggc tat ttc tac cca atc cag att gca cag tat ggg tta         207
Gly Pro Gln Gly Tyr Phe Tyr Pro Ile Gln Ile Ala Gln Tyr Gly Leu
 30              35                  40                  45 agt cac tac agc aag aat cta act gaa aaa ccc cct cat ata gag gta         255
Ser His Tyr Ser Lys Asn Leu Thr Glu Lys Pro Pro His Ile Glu Val
                 50                  55                  60 tat gaa aca gca gaa gac agg gac aaa aac agc aag ccc aat gac tgg         303
Tyr Glu Thr Ala Glu Asp Arg Asp Lys Asn Ser Lys Pro Asn Asp Trp
         65                  70                  75 act gtg ccc aag ggc tgc ttt atg gct agt gtg gct gat aag tca aga         351
Thr Val Pro Lys Gly Cys Phe Met Ala Ser Val Ala Asp Lys Ser Arg
             80                  85                  90 ttc acc aat gtt aaa cag ttc att gct cca gaa acc agt gaa ggt gta         399
Phe Thr Asn Val Lys Gln Phe Ile Ala Pro Glu Thr Ser Glu Gly Val
     95                 100                 105 tcc ttg caa ctg ggg aac aca aaa gat ttt att att tca ttt gac ctc         447
Ser Leu Gln Leu Gly Asn Thr Lys Asp Phe Ile Ile Ser Phe Asp Leu
110                 115                 120                 125 aag ttc tta aca aat gga agc gtg tct gtg gtt ctg gag acg aca gaa         495
Lys Phe Leu Thr Asn Gly Ser Val Ser Val Val Leu Glu Thr Thr Glu
                130                 135                 140 aag aat cag ctc ttc act gta cat tat gtc tca aat acc cag cta att         543
Lys Asn Gln Leu Phe Thr Val His Tyr Val Ser Asn Thr Gln Leu Ile
            145                 150                 155 gct ttt aaa gaa aga gac ata tac tat ggc atc ggg ccc aga aca tca         591
Ala Phe Lys Glu Arg Asp Ile Tyr Tyr Gly Ile Gly Pro Arg Thr Ser
        160                 165                 170 tgg agc aca gtt acc cgg gac ctg gtc act gac ctc agg aaa gga gtg         639
Trp Ser Thr Val Thr Arg Asp Leu Val Thr Asp Leu Arg Lys Gly Val
    175                 180                 185 ggt ctt tcc aac aca aaa gct gtc aag cca aca aga ata atg ccc aag         687
Gly Leu Ser Asn Thr Lys Ala Val Lys Pro Thr Arg Ile Met Pro Lys
190                 195                 200                 205 aag gtg gtt agg ttg att gcg aaa ggg aag ggc ttc ctt gac aac att         735
Lys Val Val Arg Leu Ile Ala Lys Gly Lys Gly Phe Leu Asp Asn Ile
                210                 215                 220 acc atc tct acc aca gcc cac atg gct gcc ttc ttc gct gcc agt gac         783
Thr Ile Ser Thr Thr Ala His Met Ala Ala Phe Phe Ala Ala Ser Asp
            225                 230                 235 tgg ctg gtg agg aac cag gat gag aaa ggc ggc tgg ccg att atg gtg         831
Trp Leu Val Arg Asn Gln Asp Glu Lys Gly Gly Trp Pro Ile Met Val
        240                 245                 250 acc cgt aag tta ggg gaa ggc ttc aag tct tta gag cca ggg tgg tac         879
Thr Arg Lys Leu Gly Glu Gly Phe Lys Ser Leu Glu Pro Gly Trp Tyr
    255                 260                 265 tcc gcc atg gcc caa ggg caa gcc att tct aca tta gtc agg gcc tat         927
Ser Ala Met Ala Gln Gly Gln Ala Ile Ser Thr Leu Val Arg Ala Tyr
270                 275                 280                 285 ctc tta aca aaa gac cat ata ttc ctc aat tca gct tta agg gca aca         975
Leu Leu Thr Lys Asp His Ile Phe Leu Asn Ser Ala Leu Arg Ala Thr
                290                 295                 300 gcc cct tac aag ttt ctg tca gag cag cat gga gtc aag gct gtg ttt        1023
Ala Pro Tyr Lys Phe Leu Ser Glu Gln His Gly Val Lys Ala Val Phe
            305                 310                 315
```

-continued

| | |
|---|---|
| atg aat aaa cat gac tgg tat gaa gaa tat cca act aca cct agc tct<br>Met Asn Lys His Asp Trp Tyr Glu Glu Tyr Pro Thr Thr Pro Ser Ser<br>320                           325                       330 | 1071 |
| ttt gtt tta aat ggc ttt atg tat tct tta att ggg ctg tat gac tta<br>Phe Val Leu Asn Gly Phe Met Tyr Ser Leu Ile Gly Leu Tyr Asp Leu<br>335                           340                       345 | 1119 |
| aaa gaa act gca ggg gaa aaa ctc ggg aaa gaa gcg agg tcc ttg tat<br>Lys Glu Thr Ala Gly Glu Lys Leu Gly Lys Glu Ala Arg Ser Leu Tyr<br>350                           355                       360                       365 | 1167 |
| gag cgt ggc atg gaa tcc ctt aaa gcc atg ctc ccc ttg tac gac act<br>Glu Arg Gly Met Glu Ser Leu Lys Ala Met Leu Pro Leu Tyr Asp Thr<br>                     370                       375                       380 | 1215 |
| ggc tca gga acc atc tat gac ctc cgg cac ttc atg ctt ggc att gcc<br>Gly Ser Gly Thr Ile Tyr Asp Leu Arg His Phe Met Leu Gly Ile Ala<br>                  385                       390                       395 | 1263 |
| ccc aac ctg gcc cgc tgg gac tat cac acc acc cac atc aat caa ctg<br>Pro Asn Leu Ala Arg Trp Asp Tyr His Thr Thr His Ile Asn Gln Leu<br>400                           405                       410 | 1311 |
| cag ctg ctt agc acc att gat gag tcc cca atc ttc aaa gaa ttt gtc<br>Gln Leu Leu Ser Thr Ile Asp Glu Ser Pro Ile Phe Lys Glu Phe Val<br>415                           420                       425 | 1359 |
| aag agg tgg aag agc tac ctt aaa ggc agc cgg gca aag cac aac<br>Lys Arg Trp Lys Ser Tyr Leu Lys Gly Ser Arg Ala Lys His Asn<br>430                           435                       440 | 1404 |
| tagagctcag aaccaaaatc ctacgtcagc ctctgctgta cacagaaact agaggctctg | 1464 |
| tgtcagcaga gcataggcac attttaaaag gctgtatact aggttttgt ggattacatc | 1524 |
| aaagtgataa atgatcctta aaaccagtct tctgagataa ttgcattcca tgggtttagt | 1584 |
| gtttagaatg tcgatggcat ttatagcaga aaagtgttta gtcagtgggc tgaatgaaga | 1644 |
| tgtttaactt ggcctcgctt atcaccctgt tcagttccac aggtagtcca gttctctcga | 1704 |
| tttgggaaag acaatggtaa gtagctcttg atggccagct gtccagcact tgtctgaaaa | 1764 |
| cttagtatgg ggctcttttta aaatgtggtt atttatgttt atgttgaaag cagactttaa | 1824 |
| aaaaataatg tgctaaaata cagtaaatat gtacttgtag cctgatagtg actgtgtgca | 1884 |
| acttttaaaaa tgattttttct tttctataaa ttaatttctt aggggtggat gagcatttgt | 1944 |
| tgtgtttgtt caagttgtta tatatggaga atattttgaa tttatggttt gcttgaagtg | 2004 |
| tataaattaa aaacacaacc agtgttcagg cttcacagtt atataatgta agcacaacta | 2064 |
| aaatgaaact tgttgactgc acaagaaatt acaaaacaga acaaaaatgt tatctgttttt | 2124 |
| atgaaactat ctacaatcag taaagatttg ataatcagta taccccctcct gtaccccccat | 2184 |
| tgtggtggtt tctttttgcc actatctcaa attttgtatt tcatttcaga ctacacttga | 2244 |
| gagttttgtc tattttgggg ggacattttg gggacatttg ggaaattttta ctataaacct | 2304 |
| agatttgatg aggaggtagt aagtttaata agcccactac cactgccttt tctagattct | 2364 |
| tttccccttt aaggaaaaat attaggtcag atattataag gattgtagca gattttttttc | 2424 |
| ctacttagat cattcttggt ctacagcttt ccaaactatt gatgtacaca aaatacatag | 2484 |
| tttttgtgta agctttcaaa cttttctggt gttttttctt tgcagttttt aattttaaat | 2544 |
| tatttcagct cttggataaa agtgatgcta ctatattagc tgtacatgtg taatcagacc | 2604 |
| tttattttgg ttttatatcc cacataccctc acataaatag gcatcatagc cctcacaccc | 2664 |
| tgggcagtgt ctgctctagg acttaggcag taggtcagaa ctgagggagg ttgattttgc | 2724 |
| tgtctctgtt ttagtgtatg acaatacagt aaatcaatac aataacttat acagattgga | 2784 |

| | | |
|---|---|---|
| aatacgagat ccggtacttt cagaggactg agtctgacac acgcagtgca gtgtgtgtgt | 2844 |
| gacctgtatg aaatgcacat caagagcgag gtggcacctg cctgccactg catcttgcct | 2904 |
| ggacttagtc taccaacacc actcagaaat ggcaaaatgc atacatgcct ttgagcaaca | 2964 |
| tatatgttgt atcagcagcc ggaacgaaga cctacaactg acatgaaact gttagtcact | 3024 |
| aagtcgtgtc caactctttg tgacctcata gactgtagcc cgccaggctt ctttgtccat | 3084 |
| g | 3085 |

<210> SEQ ID NO 13
<211> LENGTH: 444
<212> TYPE: PRT
<213> ORGANISM: Human

<400> SEQUENCE: 13

```
Met Ser Phe Glu Gly Tyr Asn Val Glu Val Arg Asp Arg Val Lys Cys
1               5                   10                  15

Ile Ser Gly Val Glu Gly Val Pro Leu Ser Thr Gln Trp Gly Pro Gln
            20                  25                  30

Gly Tyr Phe Tyr Pro Ile Gln Ile Ala Gln Tyr Gly Leu Ser His Tyr
        35                  40                  45

Ser Lys Asn Leu Thr Glu Lys Pro Pro His Ile Glu Val Tyr Glu Thr
    50                  55                  60

Ala Glu Asp Arg Asp Lys Asn Ser Lys Pro Asn Asp Trp Thr Val Pro
65                  70                  75                  80

Lys Gly Cys Phe Met Ala Ser Val Ala Asp Lys Ser Arg Phe Thr Asn
                85                  90                  95

Val Lys Gln Phe Ile Ala Pro Glu Thr Ser Glu Gly Val Ser Leu Gln
            100                 105                 110

Leu Gly Asn Thr Lys Asp Phe Ile Ile Ser Phe Asp Leu Lys Phe Leu
        115                 120                 125

Thr Asn Gly Ser Val Ser Val Leu Glu Thr Thr Glu Lys Asn Gln
    130                 135                 140

Leu Phe Thr Val His Tyr Val Ser Asn Thr Gln Leu Ile Ala Phe Lys
145                 150                 155                 160

Glu Arg Asp Ile Tyr Tyr Gly Ile Gly Pro Arg Thr Ser Trp Ser Thr
                165                 170                 175

Val Thr Arg Asp Leu Val Thr Asp Leu Arg Lys Gly Val Gly Leu Ser
            180                 185                 190

Asn Thr Lys Ala Val Lys Pro Thr Arg Ile Met Pro Lys Lys Val Val
        195                 200                 205

Arg Leu Ile Ala Lys Gly Lys Gly Phe Leu Asp Asn Ile Thr Ile Ser
    210                 215                 220

Thr Thr Ala His Met Ala Ala Phe Phe Ala Ala Ser Asp Trp Leu Val
225                 230                 235                 240

Arg Asn Gln Asp Glu Lys Gly Gly Trp Pro Ile Met Val Thr Arg Lys
                245                 250                 255

Leu Gly Glu Gly Phe Lys Ser Leu Glu Pro Gly Trp Tyr Ser Ala Met
            260                 265                 270

Ala Gln Gly Gln Ala Ile Ser Thr Leu Val Arg Ala Tyr Leu Leu Thr
        275                 280                 285

Lys Asp His Ile Phe Leu Asn Ser Ala Leu Arg Ala Thr Ala Pro Tyr
    290                 295                 300

Lys Phe Leu Ser Glu Gln His Gly Val Lys Ala Val Phe Met Asn Lys
305                 310                 315                 320
```

-continued

```
His Asp Trp Tyr Glu Glu Tyr Pro Thr Thr Pro Ser Ser Phe Val Leu
            325                 330                 335

Asn Gly Phe Met Tyr Ser Leu Ile Gly Leu Tyr Asp Leu Lys Glu Thr
            340                 345                 350

Ala Gly Glu Lys Leu Gly Lys Glu Ala Arg Ser Leu Tyr Glu Arg Gly
            355                 360                 365

Met Glu Ser Leu Lys Ala Met Leu Pro Leu Tyr Asp Thr Gly Ser Gly
        370                 375                 380

Thr Ile Tyr Asp Leu Arg His Phe Met Leu Gly Ile Ala Pro Asn Leu
385                 390                 395                 400

Ala Arg Trp Asp Tyr His Thr Thr His Ile Asn Gln Leu Gln Leu Leu
                405                 410                 415

Ser Thr Ile Asp Glu Ser Pro Ile Phe Lys Glu Phe Val Lys Arg Trp
            420                 425                 430

Lys Ser Tyr Leu Lys Gly Ser Arg Ala Lys His Asn
            435                 440
```

US 6,764,844 B1

DNA SEQUENCE ENCODING A NOVEL GLUCURONYL C5-EPIMERASE

The present invention relates to an isolated or recombinant DNA sequence coding for a glucuronyl C5-epimerase capable of converting D-glucuronic acid to L-iduronic acid. The invention also relates to a process for the manufacture of such epimerase.

BACKGROUND OF THE INVENTION

Heparin and heparan sulfate are complex, sulfated glycosaminoglycans composed of alternating glucosamine and hexuronic acid residues. The two polysaccharides are structurally related but differ in composition, such that heparin is more heavily sulfated and shows a higher ratio of L-iduronic acid (IdoA)/D-glucuronic acid (GlcA) units (Kjellén, Land Lindahl, U. (1991) *Annual Review of Bio-chemistry* 60, 443–475; Salmivirta, M., Lidholt, K. and Lindahl, U. (1996) *The FASEB Journal* 10, 1270–1279). Heparin is mainly produced by connective tissue-type mast cells, whereas heparan sulfate has a ubiquitous distribution and appears to be expressed by most cell types. The biological roles of heparin and heparan sulfate are presumably largely due to interactions of the polysaccharides with proteins, such as enzymes, enzyme inhibitors, extracellular-matrix proteins, growth factors/cytokines and others (Salmivirta, M., Lidholt, K. and Lindahl, U. (1990) *The FASEB Journal* 10, 1270–1279). The ineractions tend to be more or less selective/specific with regard to carbohydrate structure, and thus depend on the amounts and distribution of the various sulfate groups and hexuronic acid units. Notably, IdoA units are believed to generally promote binding of heparin and heparan sulfate chains to proteins, due to the marked conformational flexibility of these residues (Casu, E., Petitou, M., Provasoli, M. and Sinay, P. (1988) *Trends in Biochemical Sciences* 13, 221–225).

Heparin and heparan sulfate are synthesized as proteoglycans. The process is initiated by glycosylation reactions that generate saccharide sequences composed of alternating GlcA and N-acetylglucosamine (GlcNAc) units covalently bound to peptide core structures. The resulting (GlcAβ1,4-GlcNAcal,4-)$_n$ disaccharide repeats are modified, probably along with chain elongation, by a series of enzymatic reactions that is initiated by N-deacetylation and N-sulfation of GlcNAc units, continues through C-5 epimerization of GlcA to IdoA residues, and is concluded by the incorporation of O-sulfate groups at various positions. The N-deacetylation/N-sulfation step has a key role in determining the overall extent of modification of the polymer chain, since the GlcA C-5 epimerase as well as the various O-sulfotransferases all depend on the presence of N-sulfate groups for substrate recognition. While the GlcNAc N-deacetylation and N-sulfation reactions are both catalyzed by the same protein, isolation and molecular cloning of N-deacetylase/N-sulfotransferase from different tissue sources implicated two distinct forms of the enzyme. The two enzyme types differ with regard to kinetic properties, and it has been suggested that they may be differentially involved in the biosynthesis of heparin and heparan sulfate.

SUMMARY OF THE INVENTION

The present invention provides for an isolated or recombinant DNA-sequence coding for a mammalian, including human, glucuronyl C-5 epimerase or a functional derivative thereof capable of converting D-glucuronic acid (GlcA) to L-iduronic acid (IdoA).

The invention also provides for a recombinant expression vector containing a transcription unit comprising a DNA sequence as described above, a transcriptional promoter, and a polyadenylation sequence.

The invention also provides for a process for the manufacture of a glucuronyl C-5 epimerase or a functional derivative thereof capable of converting D-glucuronic acid (GlcA) to L-iduronic acid (IdoA), comprising cultivation of a cell line transformed with the above recombinant expression vector in a nutrient medium allowing expression and secretion of said epimerase or functional derivative thereof.

Specific DNA sequences according to the invention are defined in the Sequence Listing.

Furthermore, the invention provides for a host cell transformed with such recombinant expression vector.

Finally, the invention covers a glucuronyl C-5 epimerase or a functional derivative thereof whenever prepared by the process outlined above.

BRIEF DESCRIPTION OF THE FIGURES

Sequence listing: Nucleotide sequence and the predicted amino acid sequence of the C5-epimerase.

The predicted amino acid sequence is shown below the nucleotide sequence. The numbers on the right indicate the nucleotide residue and the amino acid residue in the respective sequence. The five sequenced peptides appear in bold. The N-terminal sequence of the purified protein is shown in bold and italics. The potential N-glycosylation sites (*) are shown. The potential transmembrane region is underlined.

The epimerase cDNA was inserted into a pcDNA3 expression vector and linearized with XbaI at the 3'-end. It was then subjected to in vitro transcription-translation in a rabbit reticulocyte lysate system in the presence of [$^{35}$S] methionine, as described in "Experimental Procedures". The translation product of epimerase cDNA (Epi) has a molecular weight of ~50 kDa, by comparison with the LMW protein standard. A 118 kDa control sample of β-galactosidase (C), expressed in the same system, is shown for comparison.

Figure 2:
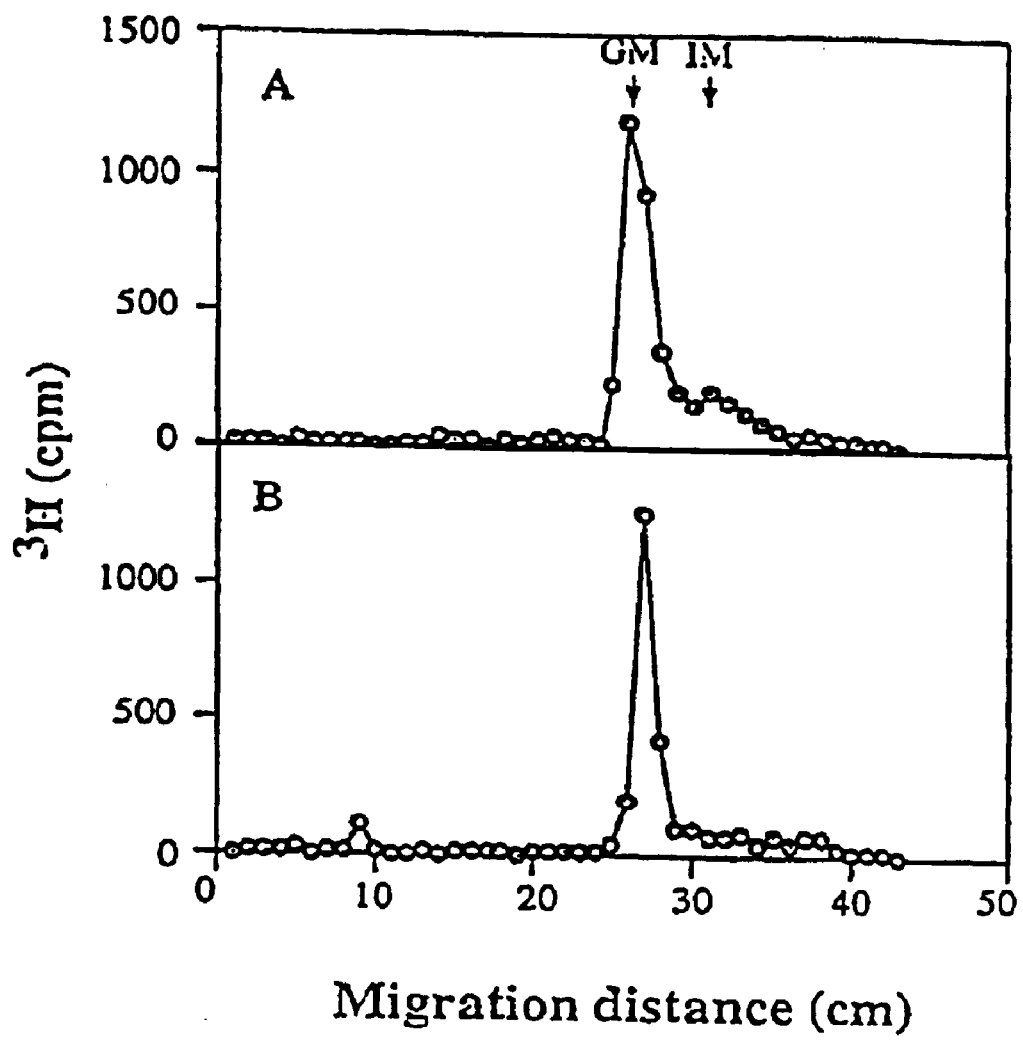

FIG. 2. Effect of the expressed C5-epimerase on N-deacetylated, N-sulfated capsular polysaccharide from *E. coli* K5.

Metabolically $^3$H-labeled K5 polysaccharide was N-deacetylated and N-sulfated, and was then incubated with (A) lysate of Sf9 cells infected with recombinant C5-epimerase; (B) lysate of Sf9 cells infected with recombinant β-glucuronidase. The incubation products were treated with HNO$_2$/NaBH$_4$, and the resultant hexuronyl-anhydromannitol disaccharides were recovered and separated by paper chromatography. The arrowheads indicate the migration positions of glucuronosyl-anhydromannitol GM) and iduronosyl-anhydromannitol (IM) disaccharide standards. For further information see "Experimental Procedures".

FIG. 3. Northern analysis of C5-epimerase mRNA expressed in bovine lung and mastocytoma cells.

Total RNA from each tissue/cell line was separated by agarose gel electrophoresis. A blot was prepared, probed with a $^{32}$P-labeled 2460-bp fragment of the epimerase cDNA clone, and finally exposed to X-ray film. (Kodak, Amersham). The arrow indicates the positions of molecular standards. For further information see "Experimental Procedures".

DETAILED DESCRIPTION OF THE INVENTION

The present invention relates to DNA sequences coding for a mammalian glucuronyl C5-epimerase or a functional derivative thereof, such epimerase or derivative being capable of converting D-glucuronic acid (GlcA) to L-iduronic acid (IdoA). The term "mammalian" is intended to include also human varieties of the enzyme.

As used herein the definition "glucuronyl C5-epimerase or a functional derivative thereof" refers to enzymes which have the capability of converting D-glucuronic acid to L-iduronic acid. Accordingly, the definition embraces all epimerases having such capability including functional variants, such as functional fragments, mutants resulting from mutageneses or other recombinant techniques. Furthermore, the definition is intended to include glycosylated or unglycosylated mammalian glucuronyl C5-epimerases, polymorfic or allelic variants and other isoforms of the enzyme. "Functional derivatives" of the enzyme can include functional fragments, functional fusion proteins or functional mutant proteins. Such epimerases included in the present invention can have a deletion of one or more amino acids, such deletion being an N-terminal, C-terminal or internal deletion. Also truncated forms are envisioned as long as they have the conversion capability indicated herein.

Operable fragments, mutants or truncated forms can suitably be identified by screening. This is made possible by deletion of for example N-terminal, C-terminal or internal regions of the protein in a step-wise fashion, and the resulting derivative can be analyzed with regard to its capability of the desired conversion of D-glucuronic acid to L-iduronic acid. If the derivative in question operates in this capacity it is considered to constitute a functional derivative of the epimerase proper.

Examples of useful epimerases are proteins having the sequence as shown in the sequence listing or substantially as shown in the sequence listing and functional portions thereof.

EXPERIMENTAL PROCEDURES

The invention is drawn to an isolated or recombinant DNA sequence coding for a mammalian, including human, glucuronyl C5-epimerase or a functional derivative of said DNA sequence, capable of converting D-glucuronic acid (GlcA) to L-iduronic acid (IdoA) constituted by a nucleotide sequence comprising nucleotide residues 1 to 1404, inclusive, as depicted in the sequence listing. The invention is further drawn to said isolated or recombinant DNA sequence comprising nucleotide residues 73 to 1404, inclusive, as depicted in the sequence listing.

The invention is also drawn to a recombinant expression vector containing a transcription unit comprising the isolated or recombinant DNA sequences of the invention, a transcriptional promoter, and a polyadenylation sequence. The invention also is drawn to a recombinant expression vector comprising the isolated or recombinant DNA sequences of the invention, characterized in that the vector is a Baculovirus. Also included in the invention is a host cell transformed with the recombinant expression vector disclosed herein.

A process for the manufacture of a glucuronyl C5-epimerase or a functional derivative thereof capable of converting D-glucuronic acid (GlcA) to L-iduronic acid (IdoA), comprising the cultivation of a host cell transformed with the recombinant expression vector of the invention, in a nutrient medium allowing expression and secretion of said epimerase or functional derivative thereof is also included in the invention. The glucuronyl C5-epimerase or a functional derivative thereof prepared by the process disclosed in the invention, is also included.

Peptide Purification and Sequencing

The 52 kDa epimerase protein (~1 $\mu$g), purified from a detergent extract of bovine liver by chromatography on O-desulfated heparin-SEPHAROSE, RED-SEPHAROSE, Phenyl-SEPHAROSE, and Concanavalin A-SEPHAROSE (Campbell, P., Hannesseon, H. H., Sandbäck, D., Rodén, L., Lindahl, U and Li, J-p. (1994) *J Biol Chem* 269, 26953–26958), was subjected to direct N-terminal sequencing using a model 470A protein sequenator (Applied Biosystems) equipped with an on-line 120 phenylthiohydantoin analyzer (Tempst, P., and Riviere, L. (1989) *Anal. Biochem.* 183, 290–300). Another sample (~1 $\mu$g) was applied to preparative (12%) SDS-PAGE and was then transferred to a PVDF membrane. After staining the membrane with Coomassie Blue, the enzyme band was excised. Half of the material was submitted to direct N-terminal sequence analysis, whereas the remainder was digested with Lys-C (0.0075 U; Waco) in the presence of 1% RTX-100/ 10% acetonitrile/100 mM Tris-HCL, pH 8.0. The generated peptides were separated on a reverse phase C4-column, eluted at a flow rate of 100 $\mu$l/min with a 6-ml 10–70% acetonitrile gradient in 0.1% trifluoroacetic acid, and detected with a 990 Waters diode-array detector. Selected peptides were then subjected to sequence analysis as described above.

Probes for Screening

Total RNA was extracted from bovine liver according to the procedures of Sambrook et al. (1989). Single-stranded cDNA was synthesized by incubating ~5 $\mu$g of bovine liver total RNA (denatured at 65° C., 3 min) with a reaction mixture containing 1 unit RNAse inhibitor (Perkin-Elmer Corp.), 1 mM of each dNTP, 5 $\mu$M random nucleotide hexamer and 1.25 units of murine leukemia virus reverse transcriptase (Perkin-Elmer Corp.) in a buffer of 10 mM Tris-HCL, pH 8.3. The mixture was kept at 42° C. for 45 min and then at 95° C. for 5 min. Degenerated oligonucleotide primers were designed based on the amino-acid sequence determined for one of the internal peptides derived from the purified epimerase (Table 1). Single-stranded bovine liver cDNA was applied to PCR together with 100 pmols of primers 1 (sense) and 3 (antisense), in a total-volume of 100 $\mu$l containing 1 $\mu$l of 10% Tween 20, 6 mM MgCl$_2$, 1 mM of each dNTP, and 2.5 units TAQ polymerase (Pharmacia Biotech) in a buffer of 10 mM Tris-HCL, pH 9.0. The reaction products were separated on a 12% polyacrylamide gel. A ~100-bp band was cut out from the gel and reamplified using the same PCR conditions. After an additional polyacrylamide gel electrophoresis, the product was isolated and sequenced, yielding a 108-bp sequence. This PCR product was subcloned into a pUC119 plasmid. The DNA fragment cleaved from the plasmid was labeled with [$^{32}$P] dCTP (DuPont NEN) using a Random Primed DNA Labeling Kit (Boehringer Mannheim).

Screening of cDNA Library

A bovine lung cDNA library constructed in a 1gt10 vector (Clontech) was screened with the 108-bp PCR fragment as hybridizing probe. The nitrocellulose replicas of the library plaques were prehybridized in 6×SSC, 5×Denhart's solution containing 0.1% SDS and 0.1 mg/ml denaturated salmon DNA for 2 hours at 65° C. Hybridization was carried out at 42° C. in the same solution containing $^{32}$P-labeled probe for 16–18 hours. The filters were washed two times with 2×SSC, 0.5% SDS and two times with 0.5×SSC, 1% SDS at the same temperature. The library was repeatedly screened twice under the same conditions. Finally, the entire cDNA phage library was subjected to PCR amplification using the 1gt10 forward and reverse primers (Clontech) with a epimerase cDNA specific primer (SEQ ID NO: 1) (5'-GCTGATTCTTTTCTGTC-3').

Subcloning and Sequencing of cDNA Inserts cDNA inserts, isolated by preparative agarose gel electrophoresis (Sambrook et al, 1989) after EcoRI restriction cleavage of recombinant bacteriophage DNA, were subcloned into a pUC119 plasmid. The complete nucleotide sequence was determined independently on both strands using the dideoxy chain termination reaction either with [$^{35}$S]dATP and the modified T7 polymerase (SEQUENASE version 2.0 DNA sequencing Kit; U. S. Biochemical Corp.) or the ALF™ System (Pharmacia Biotech). DNA sequences were compiled and analyzed using the DNASTAR™ program (Lasergene).

Polyclonal Antibodies and Immunodetection

A peptide corresponding to residues 77–97 of the deduced epimerase amino-acid sequence was chemically synthesized (Åke Engstöm, Department of medial and Physiological Chemistry, Uppsala University, Sweden), and was then conjugated to ovalbumin using glutaraldehyde (Harlow, E. and Lane, D., (1989) in Antibodies: A laboratory Manual, pp 78–79, Cold Spring Harbor, N.Y.). A rabbit was immunized with the peptide conjugates together with Freund's adjuvant. After 6 boosts (each with 240 µg conjugated peptide) blood was collected and the serum recovered. The antibody fraction was further purified on a Protein A-SEPHAROSE column (Pharmacia Biotech), and used for immunoblotting.

Samples of GlcA C5-epimerase were separated under denaturing conditions by 12% SDS-PAGE, and were then transferred fo a nitrocellulose membrane (HYBOND™ ECL). ECL immunoblotting was performed according to the protocol of the manufacturer (Amersham). Briefly, the membrane was first treated with blocking agent, then incubated with purified antibody, and finally incubated with the peroxidase labeled anti-rabbit antibody. After adding the ECL reagent, the light emitted by the chemical reaction was detected to HYPERFILM™ ECL for 30–60 sec.

Northern Blot Hybridization

Bovine liver and lung total RNA was prepared according to Sambrook, J., Fritsch, E. F. and Maniatis, T. (1989) *Molecular Cloning: A Laboratory Manual,* Cold Spring Harbor Laboratory, Cold Spring Harbor N.Y.), and mouse mastocytoma (MCT) total RNA was extracted from a tumor cell line (Montgomery, R. I., Lidholt, K., Flay, N. W., Liang, J., Verter, B., Lindahl, U. and Esko, J. D. (1992) *PNAS* 89, 11327–11331) as described by Chromezynski and Sacci (1987). Total RNA from each tissue (~20 µg samples) was denatured in 50% formamide (v/v), 5% formaldehyde, 20 mM Mops buffer, pH 7.0, at 65° C. for 5 min. The denatured RNA was separated by electrophoresis in 1.2% agarose gel containing 5% formaldehyde (v/v), and was then transferred to a HYBOND N$^+$nylon membrane (Amersham). The RNA blot was pre-hybridized in EXPRESSHYB Hybridization Solution (Clontech) at 65° C. for 1 h, and subsequently hybridized in the same solution with a [$^{32}$P]dCTP-labeled DNA probe (a 2460 bp fragment including the 5'-end of the cDNA clone; see the sequence listing). The membrane was washed in 2×SSC, 0.5% SDS at the same temperature for 2×15 min and in 0.5×SSC, 0.5% SDS for 2×5 min. The membrane was exposed to Kodak X-ray film at −70° C. for 24 h.

In Vitro Translation

The 3-kb GlcA C5-epimerase clone, inserted in a pcDNA3 expression vector (Invitrogen) was linearized at the 3'-end by restriction enzyme XbaI. In vitro translation was carried but with a Linked T7 transcription-translation system (Amersham) according to the instructions of the manufacturer. The corresponding mRNA generated by incubation of 0.5pg linearized plasmid DNA with a T7 polymerase transcription mix (total volume, 10 µl; 30° C.; 15 min) was mixed with an optimized rabbit reticulocyte lysate containing 50 µCi [$^{35}$S]methionine (total volume, 50 µl), and further incubated at 30° C. for 1 h. A sample (5 µl) of the product was subjected to 12% SDS-PAGE. The gel was directly exposed to a Kodak X-ray film. After exposure, the applied protein molecular standards (LMW Molecular Calibration Kit, Pharmacia Biotech) were visualized by staining the gel with Coomassie Blue.

Expression of the GlcA C5-Epimerase

The GlcA C5-epimerase was expressed using a BacPAK8™ Baculovirus Expression System (Clontech), according to the instructions by the manufacturer. Two oligonucleotides, one at the 5'-end of the cDNA clone (1–17 bp, sense) and the other at the 3'-end of the coding sequence (1387–1404 bp, antisense), were used to PCR amplify the coding sequence of the C5-epimerase cDNA clone. The resulting fragment was cloned into the BacPAK8 vector. Sf9 insect cells, maintained in Grece's Insect Medium (GibcoBRL) supplemented with 10% fetal calf serum and penicillin/streptomycin, were then cotransfected by the C5-epimerase construct along with viral DNA. Control transfections were performed with constructs of a β-glucuronidase cDNA construct included in the expression kit, and a mouse cDNA coding for the GlcNAc N-deacetylase/N-sulfotransferase implicated in heparin biosynthesis (Eriksson, I., Sandbäck, D., Ek, B., Lindahl, U. and Kjellén, K. (1994) *J. Biol. Chem.* 269, 10438–10443; Cheung, W F., Eriksson, I., Kusche-Gullberg, M., Lindahl, U. and Kjellén, L. (1996) *Biochemistry* 35, 5250–5256). Single plaques of each co-transfected recombinant were picked and propagated. Two Petri dishes (60-mm) of Sf9 cells were infected by each recombinant virus stock and incubate at 27° C. for 5 days. The cells from one dish were used for total RNA extraction and Northern, analysis performed as described above. Cells from the other dish were lysed in a buffer of 100 mM KCl, 15.mM EDTA, 1% Triton X-100, 50 mM HEPES, pH 7.4, containing 1 mM PMSF and 10 µg/ml pepstatin A. Supernatants of cell lysates as well as conditioned media were analyzed for epimerase activity. Protein contents of the cell lysates were estimated by the method of Bradford (1976) or by the BCA reagent procedure (Smith, P. K., Krohn, R. I., Hermanson, G. T., Mallia, A. K., Gartner, F. H., Provenzano, M. D., Fujimoto, E. K., Goeke, N. M., Olson, B. J. and Klenk, D. C. (1985) *Anal. biochem* 150, 76–85).

Demonstration of GlcA C5-epimerase activity

Epimerase activity was assayed using a biphasic liquid scintllation counting procedure, essentially as described by Campbell et al. (1994) above. The reaction mixtures, total volume 55 µl, contained 25 µl cell lysate or medium, 25 µl of 2× epimerase assay buffer (20 mM HEPES, 30 mM EDTA, 0.02% Triton X-100, 200 mM KCl, pH 7.4) and 5 µl of substrate (10,000 cpm $^3$H). The substrate was a chemically N-deacetylated and N-sulfated polysaccharide, obtained from *E. coli* K5 according to the procedure of Campbell et al. (1994), except that D-[5-$^3$H]glucose was substituted for D-[1-$^3$H]glucose.

Enzymatic conversion of D-glucuronic to L-iduronic acid was demonstrated using the metabolically 1-$^3$H-labeled substrate (N-deacetylated, N-'sulfated capsular polysaccharide from *E. coli* K5) and the analytical procedure described by Campbell et al. (1994). A sample (~20 µg; 200,000 cpm of $^3$H) of the modified polymer was incubated with 250 µl of cell lysate in a total volume of 300 µl epimerase assay buffer at 37° C. for 6 hours. The incubation was terminated by heating at 100° C. for 5 min. The sample was mixed with 50 µg of carrier heparin and reacted with nitrous acid at pH 1.5 (Shively, J., and Conrad, H. E. (1976) Biochemistry 15, 3932–3942), followed by reduction of the products with NaBH$_4$. The resultant hexuronyl-anhydromannitol disaccharides were recovered by gel chromatography on a column: (1×200 cm) of Sephadex G-15 in 0.2 M NH$_4$ HCO$_3$, lyophilized, and subjected to paper chromatography on Whatman No. 3 MM paper in ethyl acetate/acetic acid/water (3:1:1).

Results

Generation of a Probe and Screening of cDNA Library

Amino acid sequence data for the ~-52 kDa protein were obtained by digesting highly purified epimerase with lysine-specific protease, followed by separation of the generated peptides on a reverse phase column. The five most prominent peptides were isolated and subjected to amino-acid sequencing (Table I). One of the peptides (peptide 1) was found to correspond to the N-terminal sequence of the native protein. The sequence of the largest peptide obtained (peptide 5 in Table I), was used to design two sense and one antisense degenerate oligonucleotide primers, as shown in Table I. A DNA probe was produced by PCR using primers 1 and 3 with bovine liver cDNA as template. The resultant ~100 bp DNA fragment was purified by polyacrylamide gel electrophoresis, reamplified using the same primers, and finally isolated by electrophoresis. The identity of the product was ascertained by "nested" PCR, using primers 2 and 3, which yielded the expected ~60 bp fragment (data not shown). Moreover, sequencing of the larger (108 bp) DNA fragment gave a deduced amino-acid sequence identical to that of the isolated peptide (Table I).

The 108-bp PCR product was labeled with [$^{32}$P]dCTP and used for screening of a bovine lung 1gt10 library. One hybridizing clone, containing a 3-kb insert, was identified. Repeated screening of the same library yielded two additional positive clones, both of which were of smaller size Subsequent sequencing showed both of the latter clones to be contained within the 3.0-kb species (data not shown). The 3-kb clone was sequenced through both strands and was found to contain altogether 3073 bp; an additional 12-bp sequence was added at the 5'-end through characterization of a separate clone obtained by PCR amplification of the phage library (see "Experimental Procedures").

Characterization of cDNA and predicted protein structure

The total cDNA sequence identified, in all 3085 bp, contains an open reading frame corresponding to 444 amino-acid residues (SEQ ID NO: 13). Notably, the coding region (1332 bp) is heavily shifted toward the 5'-end of the available cDNA, and is flanked toward the 3'-end by a larger (1681 bp). noncoding segment. The deduced amino-acid sequence corresponds to a 49,905 dalton polypeptide. All of the five peptides isolated after endo-peptidase digestion (Table I) were recognized in the primary structure deduced from the cDNA (SEQ ID NO: 12). One of these peptides (peptide 1) is identical to the N-terminus of the isolated liver protein. This peptide was found to match residues 74–86 of the deduced polypeptide sequence (SEQ ID NO: 13). The enzyme isolated from bovine liver thus represents a truncated form of the native protein.

Figure 1:
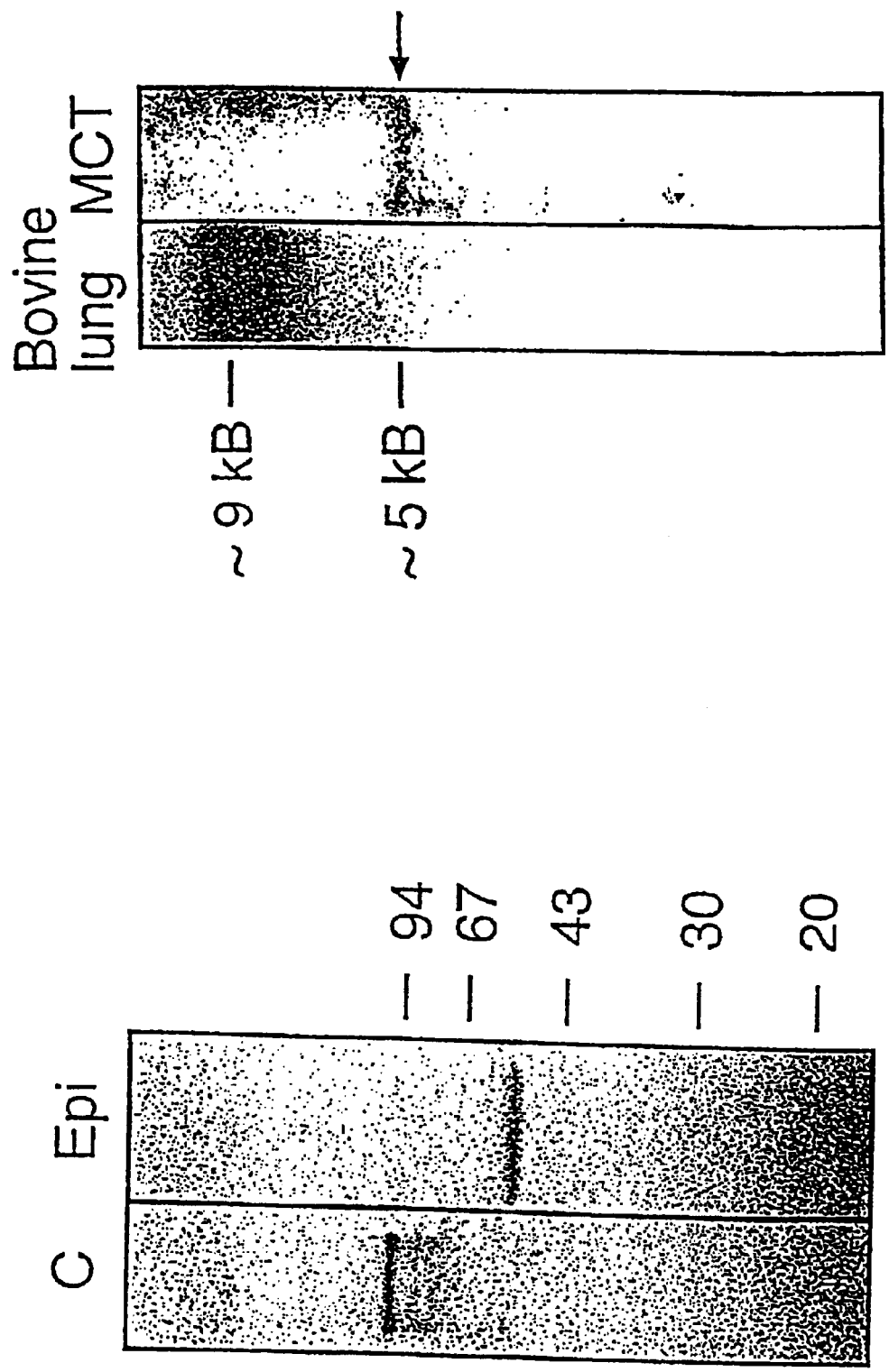
FIG. 1. In vitro transcription-translation.

Generation of mRNA from an expression vector inserted with the 3-kb cDNA clone, followed by incubation of the product with rabbit reticulocyte lysate in the presence of [$^{35}$S] methionine, resulted in the formation of a distinct labeled protein with an estimated M$_r$ of ~50 kDa (FIG. 1). This product was recognized in immunoblotting (data not shown) by polyclonal antibodies raised against a synthetic peptide corresponding to residues 77–79 (SEQ ID NO: 13) of the deduced amino-acid sequence. The same antibodies also reacted with the isolated ~52 kDa bovine liver protein (data not shown). These observations establish that the 3-kb cDNA is derived from the transcript that encodes the isolated ~52 kDa bovine liver protein.

The cDNA structure indicates the occurrence of 3 potential N-glycosylation sites (Table III). Sugar substituents may be important for the proper folding and catalytic activity of the enzyme, since the protein expressed in bacteria (which also gave a strong Western signal towards the polyclonal antibodies raised against the synthetic peptide; data not shown) was devoid of enzymatic activity. A potential transmembrane region is underlined in Table III. The predicted protein contains two cystein residues, only one of which occurs in the isolated (truncated) protein. Since NEM was inhibitory to epimerase activity (data not shown), this single cystein unit may be essential to the catalytic mechanism.

Functional Expression of the GlcA C5-Epimerase

A variety of expression systems were tested in attempts at generating the cloned protein in catalytically active form. A protein obtained by in vitro translation using a rabbit reticulocyte lysate system (see FIG. 1) showed no detectable epimerase activity. A construct made by inserting the 3-kb cDNA into a pcDNA3 vector (Invitrogen) failed to induce MRNA formation (or translation) in any of the cell lines tested (human embryonic kidney (293), COS-1 or CHO cells)\(data not shown). We also attempted to express the enzyme in a bacterial pET system (Novagen). The transformed bacteria yielded appreciable amounts of immunoreactive protein which, however, lacked detectable enzyme activity (data not shown).

Cotransfection of epimerase recombinant with baculovirus into Sf9 insect cells resulted in the generation of abundant GlcA C5-epimerase activity (Table II). In two separate experiments, the lysates from cells infected with the same epimerase recombinant virus stock showed >10-fold higher enzyme activities, on a mg protein basis, than the corresponding fractions from cells infected with control recombinant virus stock. The conditioned media of cells infected with epimerase recombinant showed 20–30-fold higher enzyme activities than the corresponding fractions from cells infected with control plasmid virus stock. Transfections with cDNA encoding other enzymes, such as a β-glucuronidase, or the mouse mastocytoma GlcNAc N-deacetylase/N-sulfotransferase involved in heparin biosynthesis (Eriksson et al., 1994), did not significantly increase the epimerase activity beyond control levels. Notably, the higher $^3H_2O$ release recorded for control samples as compared to heat-inactivated expressed enzyme (Table II) suggests that the insect cells constitutively produce endogenous C5-epimerase.

The polysaccharide substrate used for routine assays of epimerase activity was obtained by chemically N-deacetylating and N-sulfating the capsular polysaccharide [(GlcAβ1, 4-GlcNAcα1,4)n] of E. coli K5 that had been grown in the presence of [5-$^3$H]glucose. The data in Table II thus reflect the release of $^3H_2O$ from 5-$^3$H-labeled GlcA units in the modified polysaccharide, due to enzyme action (Jacobsson, I., Bäckström, G., Höök, M., Lindahl, U., Feingold, D. S., Malmström, M, and Rodén, L. (1979) J. Biol. Chem. 254, 2975–2982; Jacobsson, I., Lindahl, U., Jensen, J. W., Rodén, L., Prihar, H. and Feingold, D. S. (1984) Journal of Biological Chemistry 259, 1056–1064). More direst evidence for the actual conversion of GlcA to IdoA residues was obtained by incubating the expressed enzyme with an analogous substrate, obtained following incubation of the bacteria with [1-$^3$H]glucose. This substrate will retain the label through the epimerization reaction, and can therefore be used to demonstrate the formation of IdoA-containing disaccharide units. Following incubation with the recombinant epimerase, 21% of the hexuronic acid residues was converted to IdoA, as demonstrated by paper chromatography of disaccharide deamination products (FIG. 2). The composition of the incubated polysaccharide thus approached the equilibrium ratio of IdoA/GlcA, previously determined to ~3/7[1]).

Northern Analysis

Total RNA, from bovine liver, lung, and mouse mastocytoma, were analyzed by hybridization with a 2460-bp DNA fragment from epimerase cDNA clone as a probe. Both bovine liver and lung gave identical transcription patterns, with a dominant transcript of ~9 kb and a weak ~5 kb band (FIG. 3). By contrast, the mastocytoma RNA showed only the ~5 kb transcript.

It is to be noted that the present invention is not restricted to the specific embodiments of the invention as described herein. The skilled artisan will easily recognize equivalent embodiments and such equivalents are intended to be encompassed in the scope of the appended claims.

TABLE I

Peptide and primer sequences

A. N-terminal sequences of isolated C5 epimerase

1. PNDWXVPKGCFMA (SEQ ID NO: 2) (free solution)
2. PXDWTVPKGXF (SEQ ID NO: 3) (band excised from PVDF-membrane)

B. Peptide sequences

1. PNDXTVPK (SEQ ID NO: 4)
2. XXIAPETSEGXSLQL (SEQ ID NO: 5)
3. GGWPIMVTRK (SEQ ID NO: 6)
4. FLSEQHGV (SEQ ID NO: 7)
5. KAMLPLYDTGSGTIYDLRHFMLGIAPNLAXWDYHTT (SEQ ID NO: 8)

| primer 1 (sense) | primer 2 (sense) | primer 3 (antisense) |
|---|---|---|

| | Degeneracy |
|---|---|
| C. Primer[a] | |
| 1 (S) 5'-cc gaattcAARGCNATGYTNCCNTY-3'[b] (SEQ ID NO 9) | 384 |
| 2 (S) 5'-cc gaattcGAYYTNMGNCAYTTYATG-3' (SEQ ID NO 10) | 288 |
| 3 (AS) 5'-cc ggatccGTNGTRTGRTARTCCCA-3' (SEQ ID NO: 11) | 32 |

[a](R, A or G; Y, T or C; M, C or A; N, A or C or G or T)
[b](cc, clamp; gaatcc, EcoRI restriction site; ggatcc, BamHI restriction site

TABLE II

Expression of HexA C5-epimerase in Sf9 cells

Sf9 cells (1 × 10$^6$ in 4 ml medium) were seeded in 60-mm Petri dishes and incubated for three hours at 27° C. After the cells were attached, the medium was removed, and 200 μl of recombinant virus stock was added to infect the cells at room temperature for 1 h. The virus suspension was aspirated and 4 ml of medium was added to each dish. The cells were incubated at 27° C. for 5 days. The medium was transferred into a steril tube and centrifuged. The cells were collected, washed twice with PBS and lysed with 300 μl of homogenization buffer as described under "Experimental Procedures". Aliquots (25 μl) of cell lysate and medium were assayed for epimerase activity. The activity is expressed as release of $^3$H from K5 polysaccharide per hour. The data is mean value of three independent assays.

| | Epimerase Activity | |
|---|---|---|
| Construct | Cell lysate (cpm/mg/h) | Medium (cpm/ml/h) |
| HexA C5-Epimerase-1 | 102670 ± 5540 | 45200 ± 1770 |
| HexA C5-Epimerase-2 | 123270 ± 4660 | 52610 ± 810 |
| HexA C5-Epimerase-1 (heat-inactivted) | 240 | 610 |
| N-Deacetylase/sulfotransferase | 9520 ± 620 | 1350 ± 280 |
| β-Glucuronidase | 8460 ± 1270 | 1610 ± 440 |
| BacPAK plasmid | 5150 ± 880 | 2820 ± 690 |
| Neo | 7250 ± 370 | 550 ± 120 |

TABLE III (SEQ ID NOS: 12 & 13)

```
TCCAAGCTGAATTCTCATAGCTATTCCAAAGTCTATGCACAGAGAGCCCCTTATCACCCT      60

GATGGTGTGTTTATGTCCTTTGAAGGCTACAATGTGGAAGTCCGAGACAGAGTCAAGTGC     120
           M   S   F   E   G   Y   N   V   E   V   R   D   R   V   K   C    16

ATAAGTGGGGTTGAAGGTGTACCTTTATCTACACAGTGGGGACCTCAAGGCTATTTCTAC     180
 I   S   G   V   E   G   V   P   L   S   T   Q   W   G   P   Q   G   Y   F   Y       36

CCAATCCAGATTGCACAGTATGGGTTAAGTCACTACAGCAAGAATCTAACTGAAAAACCC     240
 P   I   Q   I   A   Q   Y   G   L   S   H   Y   S   K   N   L   T   E   K   P       56

CCTCATATAGAGGTATATGAAACAGCAGAAGACAGGGACAAAAACAGCAAGCCCAATGAC     300
 P   H   I   E   V   Y   E   T   A   E   D   R   D   K   N   S   K   P   N   D       76

TGGACTGTGCCCAAGGGCTGCTTTATGGCTAGTGTGGCTGATAAGTCAAGATTCACCAAT     360
 W   T   V   P   K   G   C   F   M   A   S   V   A   D   K   S   R   F   T   N       96

GTTAAACAGTTCATTGCTCCAGAAACCAGTGAAGGTGTATCCTTGCAACTGGGGAACACA     420
 V   K   Q   F   I   A   P   E   T   S   E   G   V   S   L   Q   L   G   N   T      116

AAAGATTTTATTATTTCATTTGACCTCAAGTTCTTAACAAATGGAAGCGTGTCTGTGGTT     480
 K   D   F   I   I   S   F   D   L   K   F   L   T   N   G   S   V   S   V   V      136

CTGGAGACGACAGAAAAGAATCAGCTCTTCACTGTACATTATGTCTCAAATACCCAGCTA     540
 L   E   T   T   E   K   N   Q   L   F   T   V   H   Y   V   S   N   T   Q   L      156

ATTGCTTTTAAAGAAAGAGACATATACTATGGCATCGGGCCCAGAACATCATGGAGCACA     600
 I   A   F   K   E   R   D   I   Y   Y   G   I   G   P   R   T   S   W   S   T      176

GTTACCCGGGACCTGGTCACTGACCTCAGGAAAGGAGTGGGTCTTTCCAACACAAAAGCT     660
 V   T   R   D   L   V   T   D   L   R   K   G   V   G   L   S   N   T   K   A      196

GTCAAGCCAACAAGAATAATGCCCAAGAAGGTGGTTAGGTTGATTGCGAAAGGGAAGGGC     720
 V   K   P   T   R   I   M   P   K   K   V   V   R   L   I   A   K   G   K   G      216

TTCCTTGACAACATTACCATCTCTACCACAGCCCACATGGCTGCCTTCTTCGCTGCCAGT     780
 F   L   D   N   I   T   I   S   T   T   A   H   M   A   A   F   F   A   A   S      236

GACTGGCTGGTGAGGAACCAGGATGAGAAAGGCGGCTGGCCGATTATGGTGACCCGTAAG     840
 D   W   L   V   R   N   Q   D   E   K   G   G   W   P   I   M   V   T   R   K      256

TTAGGGGAAGGCTTCAAGTCTTTAGAGCCAGGGTGGTACTCCGCCATGGCCCAAGGGCAA     900
 L   G   E   G   F   K   S   L   E   P   G   W   Y   S   A   M   A   Q   G   Q      276

GCCATTTCTACATTAGTCAGGGCCTATCTCTTAACAAAAGACCATATATTCCTCAATTCA     960
 A   I   S   T   L   V   R   A   Y   L   L   T   K   D   H   I   F   L   N   S      296

GCTTTAAGGGCAACAGCCCCTTACAAGTTTCTGTCAGAGCAGCATGGAGTCAAGGCTGTG    1020
 A   L   R   A   T   A   P   Y   K   F   L   S   E   Q   H   G   V   K   A   V      316

TTTATGAATAAACATGACTGGTATGAAGAATATCCAACTACACCTAGCTCTTTTGTTTTA    1080
 F   M   N   K   H   D   W   Y   E   E   Y   P   T   T   P   S   S   F   V   L      336

AATGGCTTTATGTATTCTTTAATTGGGCTGTATGACTTAAAAGAAACTGCAGGGGAAAAA    1140
 N   G   F   M   Y   S   L   I   G   L   Y   D   L   K   E   T   A   G   E   K      356

CTCGGGAAAGAAGCGAGGTCCTTGTATGAGCGTGGCATGGAATCCCTTAAAGCCATGCTC    1200
 L   G   K   E   A   R   S   L   Y   E   R   G   M   E   S   L   K   A   M   L      376

CCCTTGTACGACACTGGCTCAGGAACCATCTATGACCTCCGGCACTTCATGCTTGGCATT    1260
 P   L   Y   D   T   G   S   G   T   I   Y   D   L   R   H   F   M   L   G   I      396

GCCCCCAACCTGGCCCGCTGGGACTATCACACCACCCACATCAATCAACTGCAGCTGCTT    1320
 A   P   N   L   A   R   W   D   Y   H   T   T   H   I   N   Q   L   Q   L   L      416

AGCACCATTGATGAGTCCCCAATCTTCAAAGAATTTGTCAAGAGGTGGAAGAGCTACCTT    1380
 S   T   I   D   E   S   P   I   F   K   E   F   V   K   R   W   K   S   Y   L      436

AAAGGCAGCCGGGCAAAGCACAACTAGAGCTCAGAACCAAAATCCTACGTCAGCCTCTGC    1440
 K   G   S   R   A   K   H   N                                                      444

TGTACACAGAAACTAGAGGCTCTGTGTCAGCAGAGCATAGGCACATTTTAAAAGGCTGTA    1500

TACTAGGTTTTTGTGGATTACATCAAAGTGATAAATGATCCTTAAAACCAGTCTTCTGAG    1560

ATAATTGCATTCCATGGGTTTAGTGTTTAGAATGTCGATGGCATTTATAGCAGAAAAGTG    1620
```

TABLE III-continued

(SEQ ID NOS: 12 & 13)

| | |
|---|---|
| TTTAGTCAGTGGGCTGAATGAAGATGTTTAACTTGGCCTCGCTTATCACCCTGTTCAGTT | 1680 |
| CCACAGGTAGTCCAGTTCTCTCGATTTGGGAAAGACAATGGTAAGTAGCTCTTGATGGCC | 1740 |
| AGCTGTCCAGCACTTGTCTGAAAACTTAGTATGGGGCTCTTTTAAAATGTGGTTATTTAT | 1800 |
| GTTTATGTTGAAAGCAGACTTTAAAAAAATAATGTGCTAAAATACAGTAAATATGTACTT | 1860 |
| GTAGCCTGATAGTGACTGTGTGCAACTTTAAAAATGATTTTTCTTTTCTATAAATTAATT | 1920 |
| TCTTAGGGGTGGATGAGCATTTGTTGTGTTTGTTCAAGTTGTTATATATGGAGAATATTT | 1980 |
| TGAATTTATGGTTTGCTTGAAGTGTATAAATTAAAAACACAACCAGTGTTCAGGCTTCAC | 2040 |
| AGTTATATAATGTAAGCACAACTAAAATGAAACTTGTTGACTGCACAAGAAATTACAAAA | 2100 |
| CAGAACAAAAATGTTATCTGTTTTATGAAACTATCTACAATCAGTAAAGATTTGATAATC | 2160 |
| AGTATACCCCTCCTGTACCCCATTGTGGTGGTTTCTTTTTGCCACTATCTCAAATTTTG | 2220 |
| TATTTCATTTCAGACTACACTTGAGAGTTTTGTCTATTTTGGGGGGACATTTTGGGGACA | 2280 |
| TTTGGGAAATTTTACTATAAACCTAGATTTGATGAGGAGGTAGTAAGTTTAATAAGCCCA | 2340 |
| CTACCACTGCCTTTTCTAGATTCTTTTCCCCTTTAAGGAAAAATATTAGGTCAGATATTA | 2400 |
| TAAGGATTGTAGCAGATTTTTTTCCTACTTAGATCATTCTTGGTCTACAGCTTTCCAAAC | 2460 |
| TATTGATGTACACAAAATACATAGTTTTTGTGTAAGCTTTCAAACTTTTCTGGTGTTTTT | 2520 |
| TCTTTGCAGTTTTTAATTTTAAATTATTTCAGCTCTTGGATAAAAGTGATGGTACTATAT | 2580 |
| TAGCTGTACATGTGTAATCAGACCTTTATTTTGGTTTTATATCCCACATACCTCACATAA | 2640 |
| ATAGGCATCATAGCCCTCACACCCTGGGCAGTGTCTGCTCTAGGACTTAGGCAGTAGGTC | 2700 |
| AGAACTGAGGGAGGTTGATTTTGCTGTCTCTGTTTTAGTGTATGACAATACAGTAAATCA | 2760 |
| ATACAATAACTTATACAGATTGGAAATACGAGATCCGGTACTTTCAGAGGACTGAGTCTG | 2820 |
| ACACACGCAGTGCAGTGTGTGTGACCTGTATGAAATGCACATCAAGAGCGAGGTGGCA | 2880 |
| CCTGCCTGCCACTGCATCTTGCCTGGACTTAGTCTACCAACACCACTCAGAAATGGCAAA | 2940 |
| ATGCATACATGCCTTTGAGCAACATATATGTTGTATCAGCAGCCGGAACGAAGACCTACA | 3000 |
| ACTGACATGAAACTGTTAGTCACTAAGTCGTGTCCAACTCTTTGTGACCTCATAGACTGT | 3060 |
| AGCCCGCCAGGCTTCTTTGTCCATG | 3085 |

What is claimed is:

1. An isolated polynucleotide comprising a nucleotide sequence encoding a glucuronyl C5-epimerase capable of converting D-glucuronic acid to L-iduronic acid, the amino acid sequence of which is at least 95% identical to a reference amino acid sequence selected from the group consisting of:

(a) amino acids 25 to 444 of SEQ ID NO: 13 and
(b) amino acids 1 to 444 of SEQ ID NO: 13.

2. The isolated polynucleotide of claim 1 encoding a polypeptide comprising amino acid residues 1–144 of SEQ ID NO: 13.

3. The isolated polynucleotide of claim 1 which is DNA.

4. The isolated polynucleotide of claim 1 which is RNA.

5. The isolated polynucleotide of claim 1, wherein said isolated polynucleotide encodes a polypeptide which is a fusion protein.

6. A vector comprising the isolated polynucleotide of claim 1.

7. The vector of claim 6, wherein said vector comprises a transcription unit.

8. A host cell comprising the isolated polynucleotide of claim 1.

9. The host cell of claim 8, selected from the group consisting of Sf9 cells, *E. coli*, 293 human embryonic kidney cells, COS-1 cells and CHO. cells.

10. A method of producing a protein that comprises culturing the host cell of claim 8 under conditions such that said protein is expressed and recovering said protein.

11. An isolated polynucleotide encoding a glucuronyl C5-epimerase capable of converting D-glucuronic acid to L-iduronic acid and which hybridizes under the conditions of incubation at 65° C. in a solution comprising: 6×SSC, 5×Denhardt's solution containing 0.1% SDS and 0.1 mg/ml denatured salmon sperm DNA, followed by washing in 2×SSC and 0.5% SDS at 42° C., to a target polynucleotide encoding a polypeptide selected from the group consisting of:

(a) amino acids 25 to 444 of SEQ ID NO: 13 and
(b) amino acids 1 to 444 of SEQ ID NO: 13.

12. The isolated polynucleotide of claim 11 encoding a polypeptide comprising amino acid residues 1–444 of SEQ ID NO: 13.

13. The isolated polynucleotide of claim 11 which is DNA.

14. The isolated polynucleotide of claim 11 which is RNA.

15. The isolated polynucleotide of claim 11, wherein said polynucleotide encodes a polypeptide which is a fusion protein.

16. A vector comprising the isolated polynucleotide of claim 11.

17. The vector of claim 16, wherein said vector comprises a transcription unit.

18. A host cell comprising the isolated polynucleotide of claim 11.

19. The host cell of claim 18, selected from the group consisting of Sf9 cells, *E. coli*, 293 human embryonic kidney cells, COS-1 cells and, CHO cells.

20. A method of producing a protein that comprises culturing the host cell of claim 18 under conditions that said protein is expressed, and recovering said protein.

21. An isolated polynucleotide comprising a nucleic acid sequence which encodes a polypeptide having glucuronyl C5-epimerase activity and is capable of converting D-glucuronic acid to L-iduronic acid, and which hybridizes under the conditions of incubation at 65° C. in a solution comprising: 6×SSC, 5×Denhardt's solution containing 0.1% SDS and 0.1 mg/ml denatured salmon sperm DNA, followed by washing in 2×SSC and 0.5% SDS at 42° C., to a target polynucleotide selected from the group consisting of:

(a) nucleotides 73 to 1404 of SEQ ID NO: 12;
(b) nucleotides 73 to 3085 of SEQ ID NO: 12;
(c) nucleotides 145 to 1404 of SEQ ID NO: 12;
(d) nucleotides 145 to 3085 of SEQ ID NO: 12;
(e) nucleotides 1 to 1404 of SEQ ID NO: 12 and
(f) nucleotides 1 to 3085 of SEQ ID NO: 12.

22. The isolated polynucleotide of claim 21 comprising nucleotides 73 to 1404 of SEQ ID NO: 12.

23. The isolated polynucleotide of claim 21 comprising nucleotides 73 to 3085 of SEQ ID NO: 12.

24. The isolated polynucleotide of claim 21 comprising nucleotides 145 to 1404 of SEQ ID NO: 12.

25. The isolated polynucleotide of claim 21 comprising nucleotides 145 to 3085 of SEQ ID NO: 12.

26. The isolated polynucleotide of claim 21 comprising nucleotides 1 to 1404 of SEQ ID NO: 12.

27. The isolated polynucleotide of claim 21 comprising nucleotides 1 to 3085 of SEQ ID NO: 12.

28. The isolated polynucleotide of claim 21 which is DNA.

29. The isolated polynucleotide of claim 21 which is RNA.

30. The isolated polynucleotide of claim 21, wherein said polynucleotide encodes a polypeptide which is a fusion protein.

31. The isolated polynucleotide of claim 21, wherein said polynucleotide sequence is selected from a member of the group consisting of
   (a) nucleotides 73 to 1404 of SEQ ID NO: 12;
   (b) nucleotides 73 to 3085 of SEQ ID NO: 12;
   (c) nucleotides 145 to 1404 of SEQ ID NO: 12;
   (d) nucleotides 145 to 3085 of SEQ ID NO: 12;
   (e) nucleotides 1 to 1404 of SEQ ID NO: 12 and
   (f) nucleotides 1 to 3085 of SEQ ID NO: 12;
and wherein said isolated polynucleotide encodes a fusion protein.

32. An isolated polynucleotide which encodes an amino acid sequence which has a deletion of the N-terminal or C-terminal regions of the amino acid sequence encoded by the polynucleotide of claim 21, and wherein said polynucleotide sequence is selected from a member of the group consisting of
   (a) nucleotides 73 to 1404 of SEQ ID NO: 12;
   (b) nucleotides 73 to 3085 of SEQ ID NO: 12;
   (c) nucleotides 145 to 1404 of SEQ ID NO: 12;
   (d) nucleotides 145 to 3085 of SEQ ID NO: 12;
   (e) nucleotides 1 to 1404 of SEQ ID NO: 12 and
   (f) nucleotides 1 to 3085 of SEQ ID NO: 12.

33. A vector comprising the isolated polynucleotide of claim 21.

34. The vector of claim 33, wherein said vector comprises a transcription unit.

35. A host cell comprising the isolated polynucleotide of claim 21.

36. The host cell of claim 35, selected from the group consisting of Sf9 cells, $E.\ coli$, 293 human embryonic kidney cells, COS-1 cells and CHO cells.

37. A method of producing a protein that comprises culturing the host cell of claim 35 under conditions such that said protein is expressed, and recovering said protein.

38. An isolated polynucleotide comprising a nucleotide sequence encoding a polypeptide, comprising amino acid residues 1–444 of SEQ ID NO: 13.

39. The isolated polynucleotide of claim 38 which is DNA.

40. The isolated polynucleotide of claim 38 which is RNA.

41. The isolated polynucleotide of claim 38, wherein said polynucleotide encodes a polypeptide which is a fusion protein.

42. An isolated polynucleotide which encodes an amino acid sequence which has a deletion of the N-terminal or C-terminal regions of the amino acid sequence encoded by the polynucleotide of claim 38 and having glucuronyl C5-epimerase activity and capable of converting D-glucuronic acid to L-iduronic acid.

43. A vector comprising the isolated polynucleotide of claim 38.

44. The vector of claim 43, wherein said vector comprises a transcription unit.

45. A host cell comprising the isolated polynucleotide of claim 38.

46. The host cell of claim 45, selected from the group consisting of Sf9 cells, $E.\ coli$, 293 human embryonic kidney cells, COS-1 cells and CHO cells.

47. A method of producing a protein that comprises culturing the host cell of claim 45 under conditions such that said protein is expressed, and recovering said protein.

48. An isolated polynucleotide comprising a nucleotide sequence encoding a polypeptide, comprising amino acids 25 to 444 of SEQ ID NO: 13.

49. An isolated polynucleotide comprising nucleotides 73 to 3085 of SEQ ID NO: 12, or an isolated polynucleotide complementary to said isolated polynucleotide.

50. An isolated polynucleotide completely complementary to the one of claim 21, 22, 23, 24, 25, 26 or 27.

* * * * *

UNITED STATES PATENT AND TRADEMARK OFFICE
CERTIFICATE OF CORRECTION

PATENT NO.   : 6,764,844 B1
DATED        : July 20, 2004
INVENTOR(S)  : Lindahl et al.

It is certified that error appears in the above-identified patent and that said Letters Patent is hereby corrected as shown below:

<u>Title page,</u>
Item [75], Inventors, please delete "Jing-ping" and insert -- Jin-Ping --.

Signed and Sealed this

Eighth Day of February, 2005

JON W. DUDAS
*Director of the United States Patent and Trademark Office*